US00PP13815P39

(12) United States Plant Patent
McNeilage et al.

(10) Patent No.: US PP13,815 P3
(45) Date of Patent: May 13, 2003

(54) NEW KIWI PLANT ENTITLED 'HORTGEM TAHI'

(75) Inventors: Mark A. McNeilage, Palmerston North (NZ); Ron A. Beatson, Palmerston North (NZ); Elspeth A. MacRae, Palmerston North (NZ)

(73) Assignee: Horticulture and Food Research Institute of New Zealand, Ltd., Palmerston North (NZ)

( * ) Notice: Subject to any disclaimer, the term of this patent is extended or adjusted under 35 U.S.C. 154(b) by 0 days.

(21) Appl. No.: 09/780,809

(22) Filed: Feb. 9, 2001

(65) Prior Publication Data

US 2001/0042258 P1 Nov. 15, 2001

(30) Foreign Application Priority Data

Feb. 11, 2000 (NZ) ..... KIWI017

(51) Int. Cl.[7] ..... A01H 5/00

(52) U.S. Cl. ..... Plt./156

(58) Field of Search ..... Plt./156

*Primary Examiner*—Bruce R. Campell
*Assistant Examiner*—June Hwu
(74) *Attorney, Agent, or Firm*—Greenlee, Winner & Sullivan, P.C.

(57) ABSTRACT

A new and distinct kiwi plant of the species *Actinidia arguta* (Sieb & Zucc.) Planch. ex Miq. var. *arguta* is described. The variety results from a controlled pollination using a female *A. arguta* selection AA02-01 of unknown parentage and a male *A. arguta* selection AA13-01 of unknown parentage. Both named parents (AA02-01 and AA13-01) are unpatented. Its green hairless, edible skin, small fruit size and sweet aromatic taste distinguish the new variety.

8 Drawing Sheets

The benefits under 35 U.S.C. ' 119 are claimed with respect to New Zealand PVR Application No. KIW017, filed on Feb. 11, 2000 in New Zealand.

GENUS AND SPECIES OF PLANT CLAIMED

*Actinidia arguta.*

VARIETY DENOMINATION

'Hortgem Tahi'.

BACKGROUND OF THE INVENTION

Kiwi plants in cultivation are mainly varieties of *A. deliciosa*, particularly 'Hayward' (non-patented) although some *A. chinensis* and *A. arguta* varieties are grown. *A. deliciosa* and *A. chinensis* are closely related, whereas *A. arguta* is classified in a separate section of the genus. *A. deliciosa* and *A. chinensis* varieties have large fruit (~100 g) with hair on the skin. The main varieties in New Zealand are 'Hayward' (*A. deliciosa*) and 'Hort16A' (U.S. Plant Pat. No. 11,066) (*A. chinensis*). Fruit are usually cut and eaten with a spoon. *A. arguta* has small fruit (~10 g) with no hair on the skin. The skin is edible so these fruit can be eaten whole, like a grape.

All Actinidia species are dioecious, so female varieties have to be inter-planted with male pollenizers to ensure fruit production.

*A. arguta* vines are deciduous and tend to grow vigorously in spring and summer when rapidly-growing shoots can intertwine and tangle if not managed. Vines do best in a mild temperate climate without late spring or early autumn frosts. They produce consistent heavy crops when grown in well-drained fertile soils and given regular irrigation in dry spells.

*A. arguta* flowers in spring (late October–early December) in New Zealand. Harvest of *A. arguta* fruit may occur between early February and late March in New Zealand depending on the selection and location of plantings. Compared to *A. deliciosa* and *A. chinensis, A. arguta* fruit require more careful handling during harvest and post-harvest procedures.

SUMMARY OF THE INVENTION

The present invention is a new and distinctive kiwi plant having a small, generally spheroid shaped fruit with green hairless edible skin. This new variety is designated 'HORTGEM TAHI' and is derived from a controlled pollination of AA02-01 (non-patented), a female *A. arguta* selection of unknown parentage, with AA13-01 (non-patented), a male *A. arguta* selection of unknown parentage.

The female parent was introduced as a plant from England to New Zealand in 1955. The male parent was introduced as scionwood from Scotland to New Zealand in 1982. The provenance of both is unknown.

This new variety was created during the course of a plant breeding program, which was initiated during 1987 at HortResearch in Auckland, New Zealand. The cross was made in November 1987. Seeds were sown in autumn (March) 1988 and 129 seedlings from this cross were planted out in the field at Kumeu Research Orchard in spring (October) 1988. The seedlings first fruited in approximately February to March 1991. 20 promising female seedlings were clonally propagated into a two-site replicated trial in 1995 and 'HORTGEM TAHI' (breeding code K2D4) was selected after storage and sensory evaluation in 1998.

The new variety can be asexually reproduced as cuttings or by grafting or budding on to seedling or cutting-grown rootstocks of *A. arguta.* Trial plantings as cuttings established in 1995 at Te Puke and Nelson Research Centres and on seedling rootstocks established in 1998 at these sites have shown that the unique combination of characters come true to form and are established and transmitted through succeeding asexual propagation.

'HORTGEM TAHI' is a different species to both the unpatented 'Hayward' variety and the patented 'Hort16A' variety, so their pollenizers cannot be used. Three new *A. arguta* male pollenizers known currently by their breeding codes as B4G4 (non-patented), E4H4 (non-patented) and K1J6 (non-patented), have been selected as males for use in new plantings of 'HORTGEM TAHI'.

BRIEF DESCRIPTION OF ILLUSTRATIONS

Figure 1:
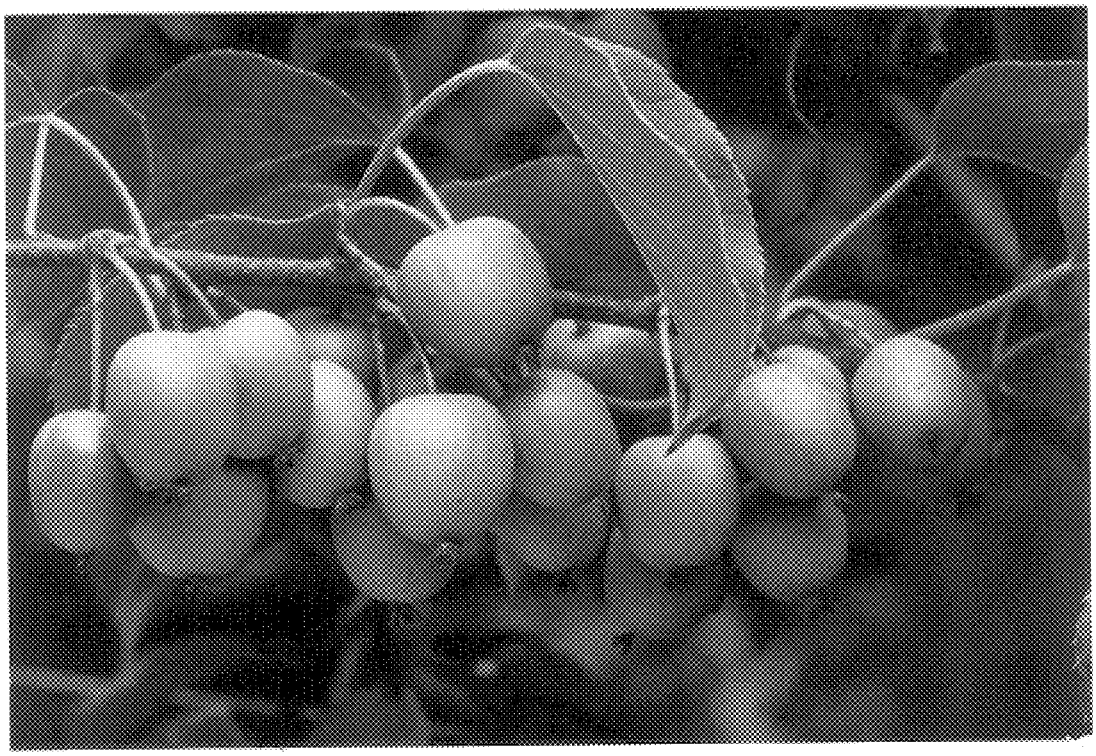
FIG. 1 shows typical fruit of the new variety in the orchard.
Figure 2:
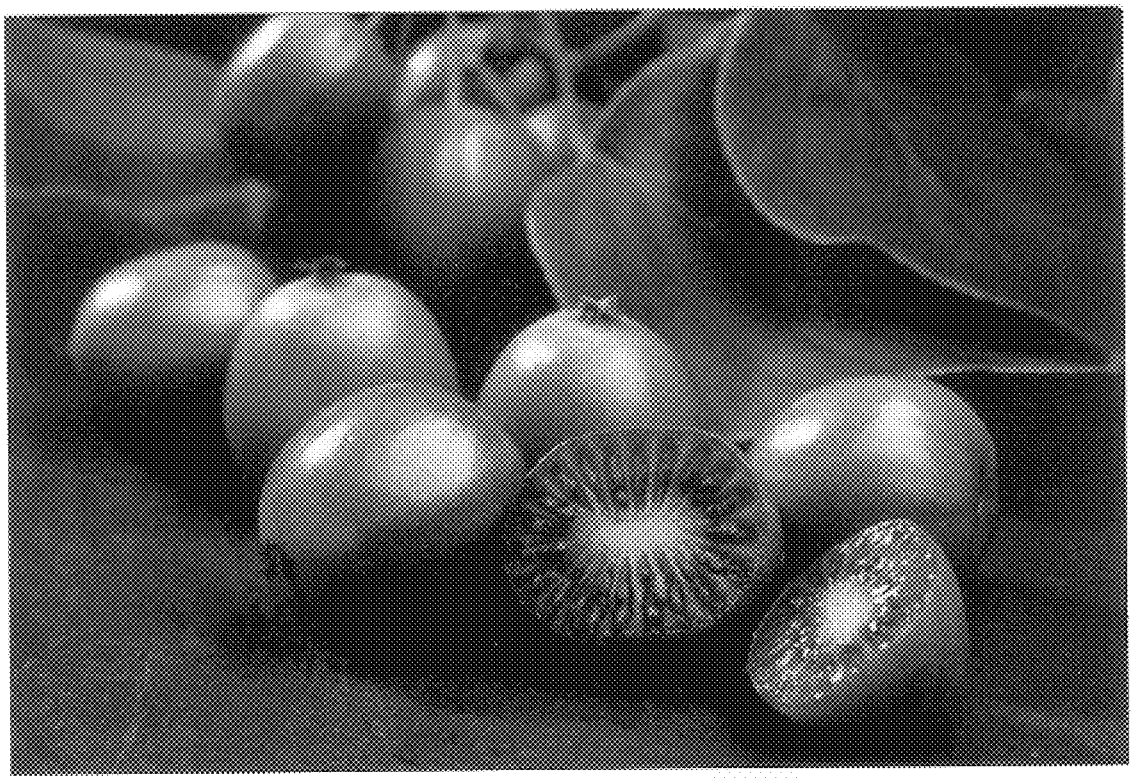
FIG. 2 shows typical fruit of the new variety in the studio.
Figure 3:
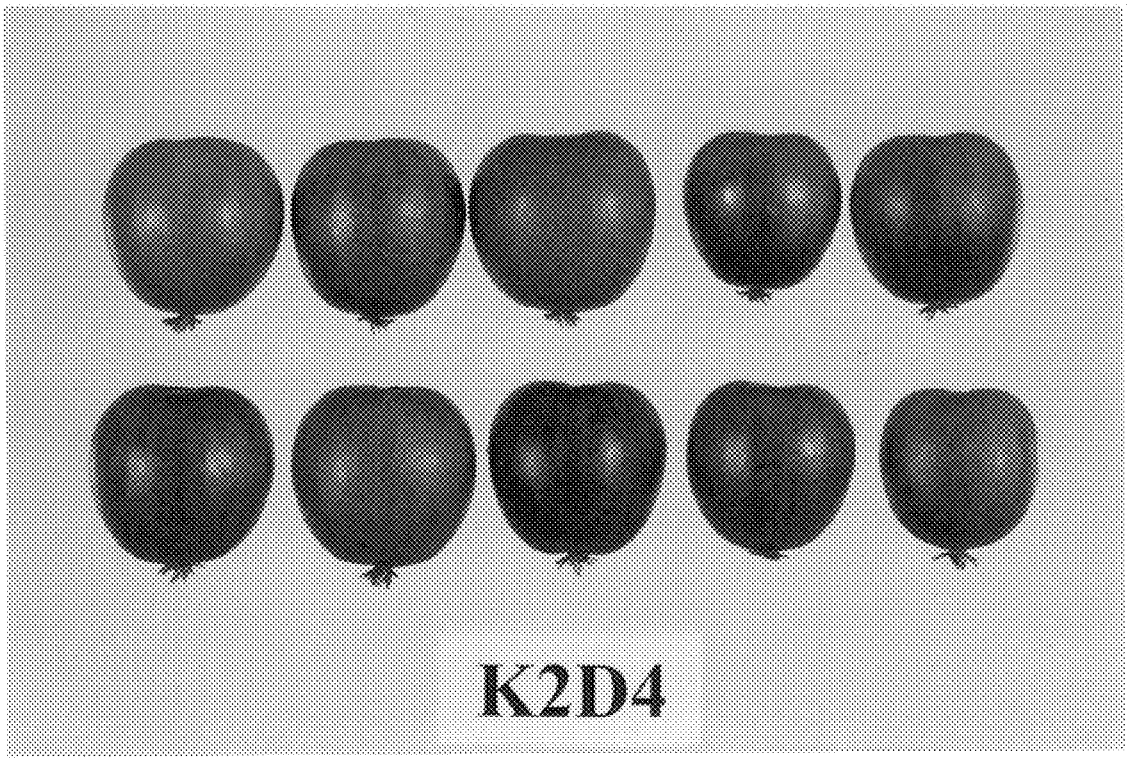
FIG. 3 shows fruit of the new variety in profile.
Figure 4:
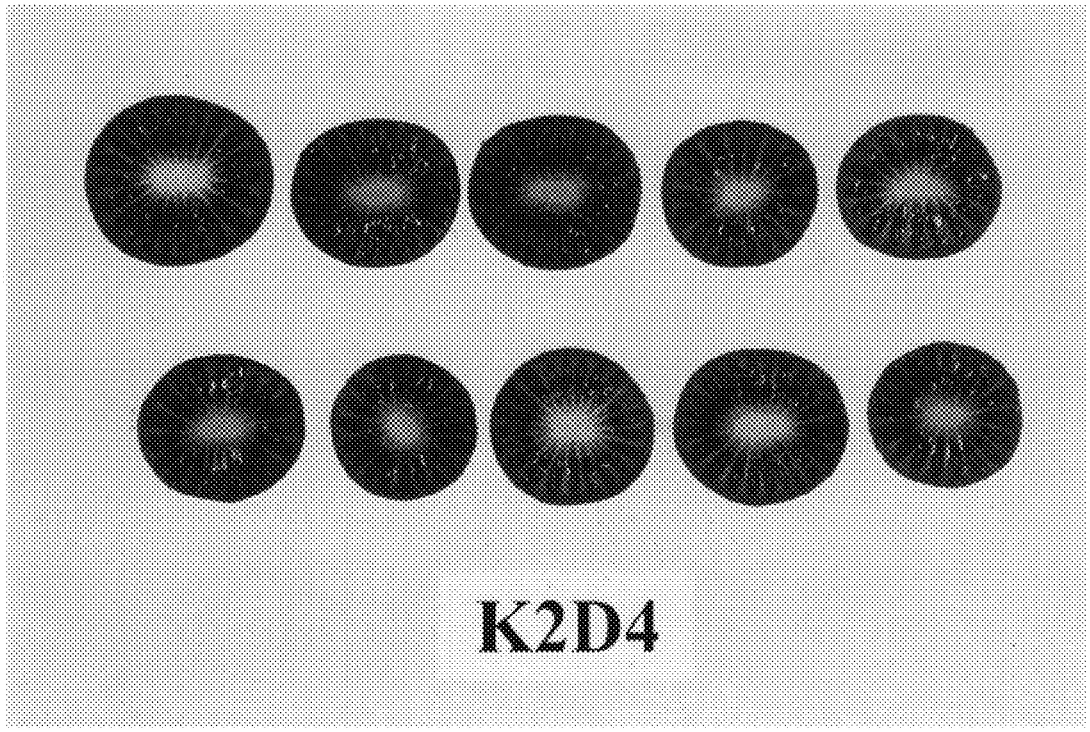
FIG. 4 shows fruit of the new variety in cross-section.
Figure 5:
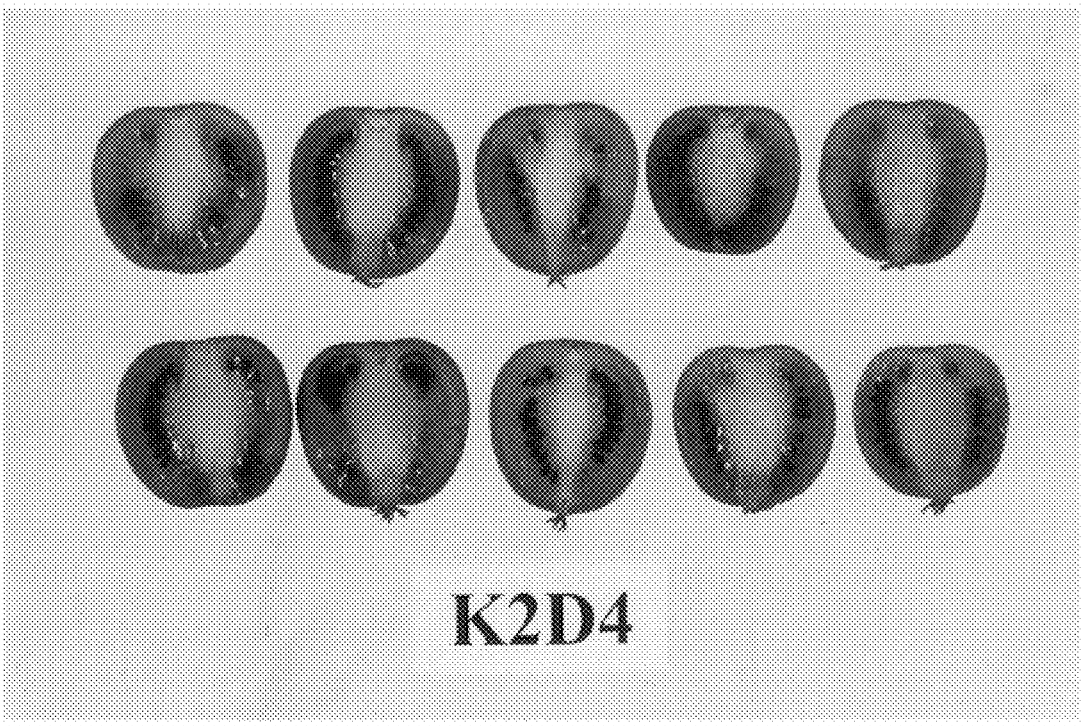
FIG. 5 shows fruit of the new variety in longitudinal section.
Figure 6:
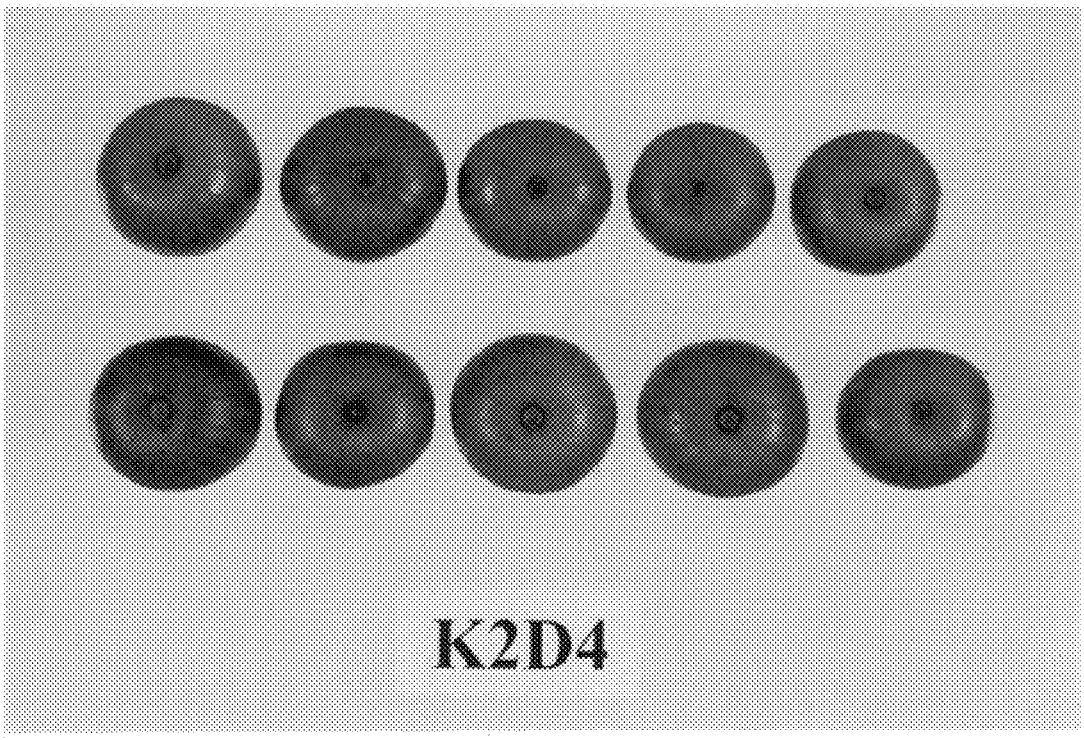
FIG. 6 shows the stem end and stem end cavity of the fruit from the new variety.
Figure 7:
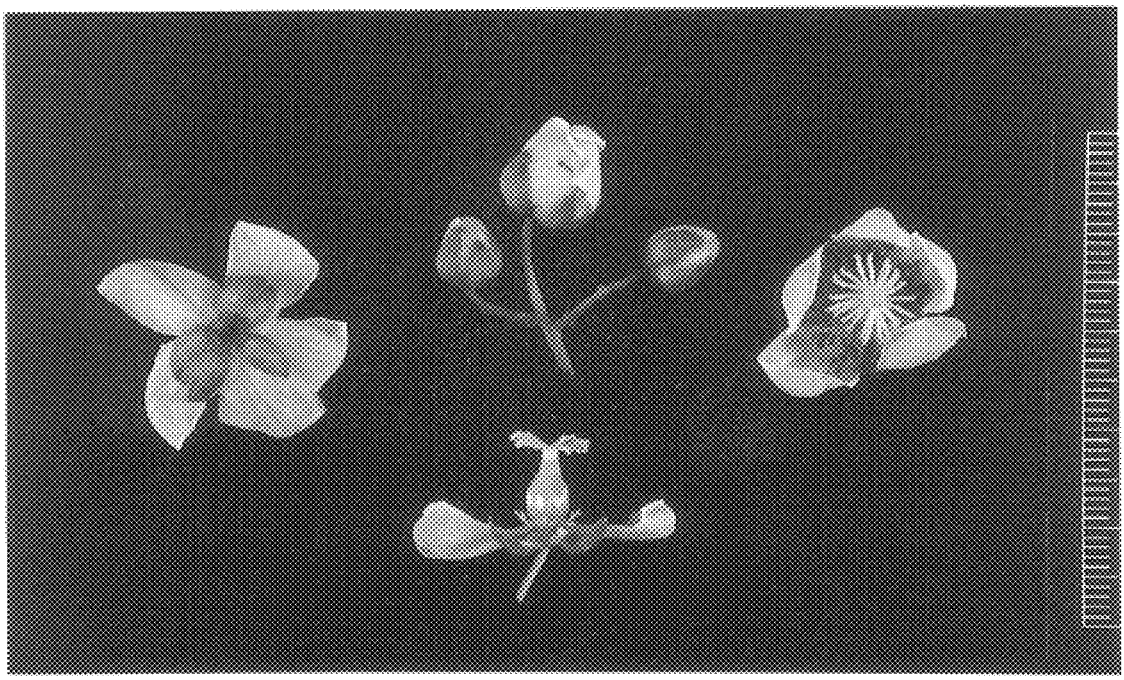
FIG. 7 shows flowers of the new variety.
Figure 8:
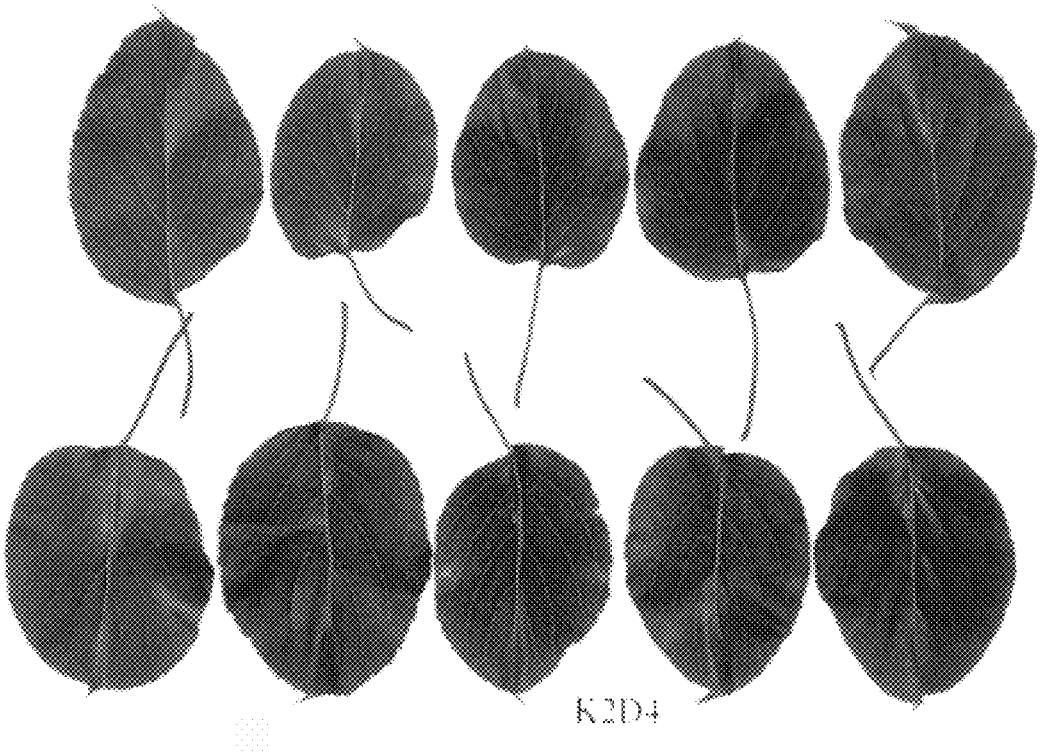
FIG. 8 shows foliage of the new variety.

Photographs of fruit from the new variety were taken after the normal harvest date. Fruit skin color may vary depending upon extent of exposure to direct sunlight.

COMPARISON TO CLOSEST VARIETY

The distinctive characteristics of this new Kiwi variety, described in detail below, were observed in 2000 at Te Puke, New Zealand. The age of the plants was 5 years from planting cutting-grown plants. 'HORTGEM TAHI' is a new type of kiwi with no close varieties available in New Zealand. The *A. deliciosa* variety 'Hayward' and the *A. chinensis* variety 'Hort16A' are different in most characters and so do not provide a useful comparison. *A. arguta* varieties are grown in other countries, e.g. 'Annanaskaya' (non-patented) in U.S.A. , but are unavailable in New Zealand.

The fruit of 'HORTGEM TAHI' is spheroid in shape with a rounded distal end. 'HORTGEM TAHI' fruit has a relatively large core proportionate to the surrounding pericarp. The flesh is green. The skin is without hairs and is a shiny green. 'HORTGEM TAHI' fruit have a high dry matter content at harvest and are sweet tasting when ripe. Fruit can be cool-stored for 12 weeks and retain eating quality.

DESCRIPTION OF THE NEW VARIETY

The new variety 'HORTGEM TAHI' is pistillate, with morphologically perfect but functionally imperfect flowers, i.e. the flowers produce only sterile pollen and thus require a pollenizer for fruit production. Three specific unpatented *A. arguta* pollenizers, designated B4G4, E4H4, K1J6, have been developed for 'HORTGEM TAHI'. Characteristics of the new variety include a short period (~3 months) between flowering and harvest, early harvest, small spheroid fruit with green hairless edible skin, green flesh and a sweet aromatic flavor. The following description are features described as they appear at the Te Puke Research Centre, New Zealand

DETAILED DESCRIPTION OF THE VARIETY

Horticultural terminology is used in accordance with revised UPOV guidelines for kiwi. All dimensions in millimeters, weights in grams (unless otherwise stated). Color chart: R.H.S. Color Chart, The Royal Horticultural Society, London ($3^{rd}$ ed. 1995).

Plant and foliage

This female (flowers imperfect) plant expresses strong vigor and is tetraploid (2n=2x=116). Tomentose hairs are present on the young shoot. Anthocyanin (red) coloration (near Red-purple 60A) of the growing tip is absent or very weak similar to the variety 'Hort16A'. Otherwise the young shoot is near Greyed-green 192B in color. The stem of the plant is thin; averaging between approximately 7 to 8 mm in diameter, with the range of diameters observed approximately 4.2 to 12.2 mm. The stem color on the exposed side ranges between near Greyed-orange 166B and near Greyed-orange 176A. The bark is smooth and absent of hairs. The lenticels are many (approximately 25–35/$cm^2$), conspicuous and near Greyed-orange 169D in color. Coloration of the leaf axil is either absent or very weak on both the young shoot and the stem. Dormant bud diameter is small; typically about 2.2 mm in diameter (ranging 0.7 to 4.0 mm). Buds are visible on the dormant cane and dormant buds are absent of hairs. The leaf scar is deep.

The blade of the mature leaf is generally broad; ovate, averaging approximately 102.3 mm in length (observed range approximately 82 to 126 mm) and averaging approximately 75.1 mm in width (observed range approximately 62 to 89 mm). The shape of the tip of the blade is caudate while the shape of the base is rounded. The arrangement of the leaf basal lobes is far apart. Puckering or blistering on the upper side of the blade is absent or very weak. The leaf margin is ciliate. The upper side of the blade of the leaf (observed for the mature leaf after petal fall) ranges between near Green 137A and near Green 139A. The lower side of the blade of the leaf (observed for the mature leaf after petal fall) ranges between near Green 138B and near Yellow-green 146B. The upper surface of the leaf exhibits medium glossiness and there is no glaucosity on the lower side of the leaf. The petiole length averages approximately 57.7 mm in length (observed range approximately 38 to 93 mm) and is largely absent of hairs. Anthocyanin (red) coloration on the upper side of the petiole is a similar medium density to the variety Hayward.

Inflorescence

The predominant number of flowers in the inflorescence is one. The pedicel length is short, averaging about 29.8 mm (observed range between approximately 24.9 and 33.8 mm) with sparse, very short, hairs. There are typically 5 sepals, although sometimes more. These are reddish brown in color, although the color fades to a lighter shade at the base (near Greyed-brown, 199D). The diameter of the terminal or king flower when fully open is small, averaging about 28.2 mm (observed range between approximately 23.2 and 31.2 mm). The petal length averages approximately 14.5 mm (observed range between approximately 12.7 and 15.7 mm) and averages approximately 13.0 mm in width (observed range approximately 11.0 and 14.6 mm). The petal length/width ratio is approximately 1.12 mm (observed range between approximately 1.02 and 1.33 mm). The mean number of petals per flower is approximately 5.4 (observed range approximately 5 to 7). The petals are arranged apart and are near Green-white 157A in color when fully open. The color is uniform over the whole petal. Fragrance is present, and is moderately strong, and sweet.

The number of stamens averages approximately 44.4 (observed range approximately 40–50). The stamen filament averages approximately 4.2 mm in length (observed range approximately 3.6 to 5.0 mm), while the anthers average approximately 3.7 mm in length (observed range approximately 3.2 to 4.2 mm). The filament color is near light green (Green 130D) similar to the variety 'Matua' (not patented). The anther is near black in color. The number of styles averages approximately 20.7 (observed range approximately 18 to 24). The styles average 4.4 mm in length (observed range approximately 4.1 to 5.2 mm). The styles are arranged in a horizontal attitude with weak curvature, and are near white (White 155C) in coloration. The length of the ovary averages 6.8 mm (observed range approximately 6.0 to 7.4 mm). The ovary is absent of hairs and is near Yellow-green 145A in color.

Fruit

The fruit are overall small in size, averaging approximately 11.1 g (observed range averaging approximately 9.5 to 12.8 g). The fruit average approximately 26.5 mm in length (observed range between approximately 23.6 and 29.4 mm) with a maximum width averaging approximately 26.8 mm (observed range approximately 24.3 to 30.3 mm) and a minimum width averaging approximately 24.3 mm (observed range approximately 21.8 to 28.0 mm). The locule number averages about 20.7 (observed range approximately 18 to 26). The peduncle length averages approximately 29.5 mm (observed range approximately 23.6 to 34.0 mm) and the peduncle width averages approximately 2.0 mm (observed range approximately 1.5 to 2.5 mm). The general shape of the fruit is spheroid although the cross-section at the median of the fruit is oblate in shape. The stylar end of the fruit is generally rounded and the shape of the shoulder on the stalk end is generally square. The fruit skin color at harvest (fruit still hard) is medium green. There is no skin color change during ripening and the skin color at maturity for consumption is between near Green 141C and near Green 143C. The fruit skin is absent of hairs.

The fruit core is large in diameter, is oblate in shape in cross-section, and is between near Yellow-green 150D and near Green-white 157B in color at harvest. There is no woody spike. Both the color of the outer pericarp, and the inner pericarp (locules), at maturity for consumption are between near Green 139B and near Green 141B. Fruit sweetness (Brix level) at maturity for consumption averages approximately 20.2% (observed range between approximately 17.2 and 22.0%). The Vitamin C content (sampled from a 45 fruit sample) averages approximately 51 mg/100 g fresh weight (observed range approximately 37 to 67 mg/100 g fresh weight). Fruit aroma is present. Seed is small (maximum averages diameter approximately 1 mm). The seed color at maturity, both in the flesh and when dry, ranges between near Greyed-orange 172B and near Greyed-orange 175C.

Cultivation

Vegetative budbreak occurs about late August in New Zeland, whilst flowering commences about mid-November. The time of fruit maturity for harvest (at nominated Brix level) occurs between approximately late February and early March in New Zealand.

Observations made on cutting-grown plants at Te Puke Research Center, New Zealand demonstrated the following horticultural characteristics:

*Cropping.*—Young vines of the new variety are precocious, beginning to bear in their second year and are expected to reach full capacity at about 7 years. The storage life of the fruit of the new variety is about 10 to 12 weeks at 0° C., if stored in unventilated containers.

*Fruit size.*—Data from harvesting all fruit from 6 vines in late February 1999 is as follows: Mean fruit weight: 10.8 g. Maximum: 12.6 g. Minimum: 9.7 g. Mean fruit number: 2087. Maximum: 3610. Minimum: 802. Mean yield: 21.96 kg. Maximum: 35.14 kg. Minimum: 8.42 kg.

These vines were about 3 years old. It is expected that for mature, well-managed vines mean fruit weight will be about 10 g., mean fruit number about 5000 fruit, and mean yield per vine about 50 kg.

No pest and disease resistance has been observed. The plant hardiness range (according to the American zone classification) has not been determined. Under New Zealand conditions, the plants are grown in areas that experience some winter cold and frost, estimated to be equivalent to the minimum temperature range of zones 8 and 9.

We claim:

1. A new and distinct kiwi plant of the species *A. arguta* substantially as described and illustrated, characterized by small spheroid fruit with green hairless edible skin and green flesh with a sweet aromatic flavor.

* * * * *

K2D4